(12) United States Patent
Steinhauser et al.

(10) Patent No.: US 8,978,450 B2
(45) Date of Patent: Mar. 17, 2015

(54) COMBINATION FLUID SENSOR SYSTEM

(75) Inventors: Louis P. Steinhauser, St. Louis, MO (US); Jacob Lindley, St. Louis, MO (US); John Paskvan, Gurnee, IL (US)

(73) Assignee: Watlow Electric Manufacturing Company, St. Louis, MO (US)

( * ) Notice: Subject to any disclaimer, the term of this patent is extended or adjusted under 35 U.S.C. 154(b) by 653 days.

(21) Appl. No.: 13/186,916

(22) Filed: Jul. 20, 2011

(65) Prior Publication Data
US 2012/0186334 A1   Jul. 26, 2012

Related U.S. Application Data

(60) Provisional application No. 61/366,642, filed on Jul. 22, 2010.

(51) Int. Cl.
G01N 25/00 (2006.01)
H05B 3/82 (2006.01)
G01N 27/12 (2006.01)
H05B 3/46 (2006.01)

(52) U.S. Cl.
CPC ............... *H05B 3/82* (2013.01); *G01N 27/123* (2013.01); *H05B 3/46* (2013.01); *H05B 2203/003* (2013.01); *H05B 2203/01* (2013.01); *H05B 2203/013* (2013.01); *H05B 2203/02* (2013.01)
USPC ....................................................... 73/61.76

(58) Field of Classification Search
USPC ....................................................... 73/61.76
See application file for complete search history.

(56) References Cited

U.S. PATENT DOCUMENTS

| | | | |
|---|---|---|---|
| 4,703,652 A | 11/1987 | Itoh et al. | |
| 6,114,176 A | 9/2000 | Edgson et al. | |
| 6,250,152 B1 | 6/2001 | Klein et al. | |
| 6,758,093 B2 | 7/2004 | Tang et al. | |
| 7,030,629 B1 | 4/2006 | Stahlamann et al. | |
| 7,064,560 B2 | 6/2006 | Yamamoto et al. | |
| 7,153,693 B2 | 12/2006 | Tajiri et al. | |
| 7,222,528 B2 | 5/2007 | Stahlamann et al. | |
| 7,287,426 B2 | 10/2007 | Frank | |
| 7,337,662 B2 | 3/2008 | Sato et al. | |
| 7,339,657 B2 | 3/2008 | Coates | |
| 7,377,185 B2 | 5/2008 | Kawanishi et al. | |
| 7,469,574 B2 | 12/2008 | Kawanishi et al. | |
| 7,499,814 B2 | 3/2009 | Nishina et al. | |
| 7,542,870 B2 | 6/2009 | Reimer et al. | |
| 7,574,900 B2 | 8/2009 | Sasanuma et al. | |

(Continued)

FOREIGN PATENT DOCUMENTS

| | | |
|---|---|---|
| EP | 1152639 | 11/2001 |
| EP | 1752762 | 2/2007 |
| WO | 0157488 | 8/2001 |

OTHER PUBLICATIONS

International Search Report and Written Opinion for PCT/US2011/044662 dated Oct. 12, 2011.

*Primary Examiner* — Hezron E Williams
*Assistant Examiner* — Rodney T Frank
(74) *Attorney, Agent, or Firm* — Brinks Gilson & Lione

(57) ABSTRACT

An apparatus for determining and controlling characteristics of a fluid is provided that includes a substrate, a heating circuit, and a sensing circuit applied on the substrate by a layered process. A control module is in communication with the heating circuit and the sensing circuit for determining, for example, type, concentration, liquid level, and temperature of the fluid, which in one form is a urea solution.

22 Claims, 18 Drawing Sheets

(56) References Cited

U.S. PATENT DOCUMENTS

| | | |
|---|---|---|
| 7,587,288 B2 | 9/2009 | Nishina et al. |
| 7,611,667 B2 | 11/2009 | Centanni |
| 7,617,672 B2 | 11/2009 | Nishina et al. |
| 7,637,148 B2 | 12/2009 | Sasanuma et al. |
| 7,658,093 B2 | 2/2010 | Nishina et al. |
| 7,665,347 B2 | 2/2010 | Sasanuma et al. |
| 7,712,363 B2 | 5/2010 | Sasanuma et al. |
| 7,722,813 B2 | 5/2010 | Inoue et al. |
| 2004/0251919 A1 | 12/2004 | Stahlmann et al. |
| 2005/0008354 A1 | 1/2005 | Cassidy |
| 2007/0006639 A1 | 1/2007 | Sasanuma et al. |
| 2007/0110618 A1 | 5/2007 | Sasanuma et al. |
| 2007/0113625 A1 | 5/2007 | Sasanuma et al. |
| 2007/0125663 A1 | 6/2007 | Sasanuma et al. |
| 2007/0169544 A1 | 7/2007 | Yamamoto et al. |
| 2007/0193345 A1 | 8/2007 | Yamamoto et al. |
| 2008/0038153 A1 | 2/2008 | Yamamoto et al. |
| 2008/0087009 A1 | 4/2008 | Nishina et al. |
| 2008/0205478 A1 | 8/2008 | Sasanuma et al. |
| 2009/0090178 A1 | 4/2009 | Sasanuma et al. |
| 2010/0003168 A1 | 1/2010 | Sasanuma et al. |
| 2010/0101307 A1 | 4/2010 | Sasanuma et al. | ns
COMBINATION FLUID SENSOR SYSTEM

CROSS-REFERENCE TO RELATED APPLICATIONS

This application claims the benefit of provisional application Ser. No. 61/366,642, filed on Jul. 22, 2010, the contents of which are incorporated herein by reference in their entirety.

FIELD

The present disclosure relates to fluid sensors and control systems, and more particularly, sensors and control systems for determining and controlling characteristics of the fluid, such as level, temperature, type, concentration, and/or contamination of a fluid.

BACKGROUND

The statements in this section merely provide background information related to the present disclosure and may not constitute prior art.

A selective reduction catalyst (SCR) may be used in exhaust systems of diesel engines to reduce NOx emissions. NO contained in the exhaust gas undergoes a reduction reaction as the exhaust gases pass through the catalyst chamber of the SCR and is reduced into nitrogen ($N_2$) and water ($H_2O$). The NO reduction reaction may be expressed in the following chemical reactions:

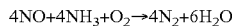

$4NO+4NH_3+O_2 \rightarrow 4N_2+6H_2O$

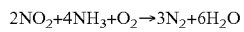

$2NO_2+4NH_3+O_2 \rightarrow 3N_2+6H_2O$

$NO+NO_2+2NH_3 \rightarrow 2N_2+3H_2O$

Liquid urea, instead of gaseous ammonia ($NH_3$), is generally used as the reductant due to toxic nature and difficulty in storage of gaseous ammonia. Liquid urea is injected upstream from the SCR and mixed with the exhaust gas. The mixture of urea and exhaust gas is absorbed onto the SCR. Urea is converted into gaseous ammonia through thermal decomposition before the reduction reaction takes place.

Urea is stored in a dedicated urea tank. The urea solution generally includes 32.5% urea and 67.5% water by weight, in part, such that a low freezing temperature can be obtained. A plurality of sensors and devices are incorporated in the urea tank to ensure that sufficient urea solution is contained in the urea tank and is in good quality for an effective NOx reduction. For example, a heating device may be required to heat the urea solution to prevent the urea solution from freezing at around 11° F. A concentration sensor may be required to monitor the concentration of the urea solution to ensure that the urea solution is not intentionally or unintentionally diluted or contaminated with other liquids. A liquid level sensor may be required to ensure that sufficient amount of urea is present in the tank. These different devices and sensors require separate control and take a significant amount of space and costs.

SUMMARY

In one form, an apparatus for determining and controlling characteristics of a fluid is provided that includes a substrate, a heating circuit and a sensing circuit applied on the substrate. The heating circuit and the sensing circuit are applied on the substrate by a layered process.

In another form, an apparatus for determining and controlling characteristics of a fluid includes a probe section, a layered heating circuit formed on the probe section and a control module. The resistance of the heating circuit changes with temperature. The control module is in communication with the heating circuit and determines at least one of concentration, temperature and level of the fluid based on a change of resistance of the heating circuit.

In still another form, a method of determining and controlling characteristics of a fluid is provided that includes energizing a heating circuit, measuring a change of resistance of the heating circuit after the heating circuit is energized, and determining concentration, temperature, and level of the fluid based on the change of resistance of the heating circuit.

Further aspects of the present disclosure will be in part apparent and in part pointed out below. It should be understood that various aspects of the disclosure may be implemented individually or in combination with one another. It should also be understood that the detailed description and drawings, while indicating certain exemplary forms of the present disclosure, are intended for purposes of illustration only and should not be construed as limiting the scope of the disclosure.

DRAWINGS

The drawings described herein are for illustration purposes only and are not intended to limit the scope of the present disclosure in any way.

It should be understood that throughout the drawings corresponding reference numerals indicate like or corresponding parts and features.

DETAILED DESCRIPTION

The following description is merely exemplary in nature and is not intended to limit the present disclosure or the disclosure's applications or uses.

Figure 1:
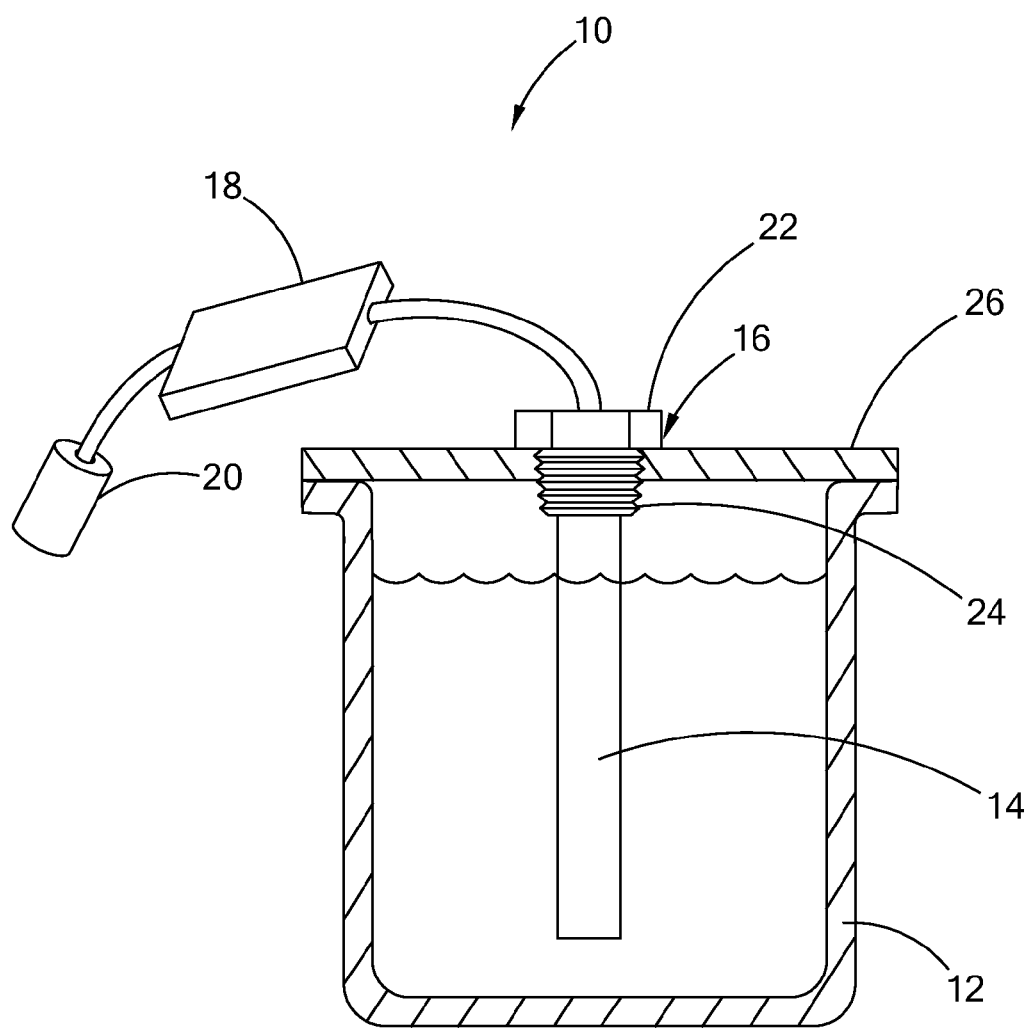
FIG. 1 is a schematic view of an apparatus and a tank in accordance with the principles of the present disclosure.

Referring to FIG. 1, an apparatus 10 constructed in accordance with the principles of the present disclosure is mounted to a tank 12 which contains a fluid, such as a urea solution. The apparatus 10 includes a plurality of devices integrated into a single unit for determining and controlling characteristics of the fluid, such as, type, level, concentration, and temperature. The apparatus 10 can also determine whether the fluid is contaminated. It is understood that the apparatus 10 may be used to detect and control characteristics of fluids other than a urea solution without departing from the scope of the present disclosure. As such, the term "fluid" shall be construed to mean all forms of matter such as liquid, gas, solid, and plasma, and thus the apparatus 10 according to the present disclosure may be employed to determine and control characteristics of any form of matter.

The apparatus 10 generally includes a probe section 14, a mounting section 16, a control module 18, and a terminal section 20. The probe section 14 has an elongated structure and is immersed in the urea solution contained in the tank 12. In one form, the mounting section 16 is configured to include a flange 22 and a screw 24 to be screwed into a screw hole 24 of a top wall 26 of the tank 12. It should be understood, however, that any number of mechanical configurations may be employed to connect the apparatus 10 to the tank 12, such as, by way of example, quick disconnects, press-fit, or adhesives/bonding, among others. The control module 18 includes a plurality of control circuits and algorithms for determining and controlling characteristics of the urea solution based on output signals from a heater and a plurality of sensors, described in greater detail below, provided on the probe section 14. The plurality of sensors may include, by way of example, a temperature sensor, a concentration sensor, and a fluid level sensor. The terminal section 20 is configured to be connected to a power source and/or a communication system (not shown).

Figure 2:
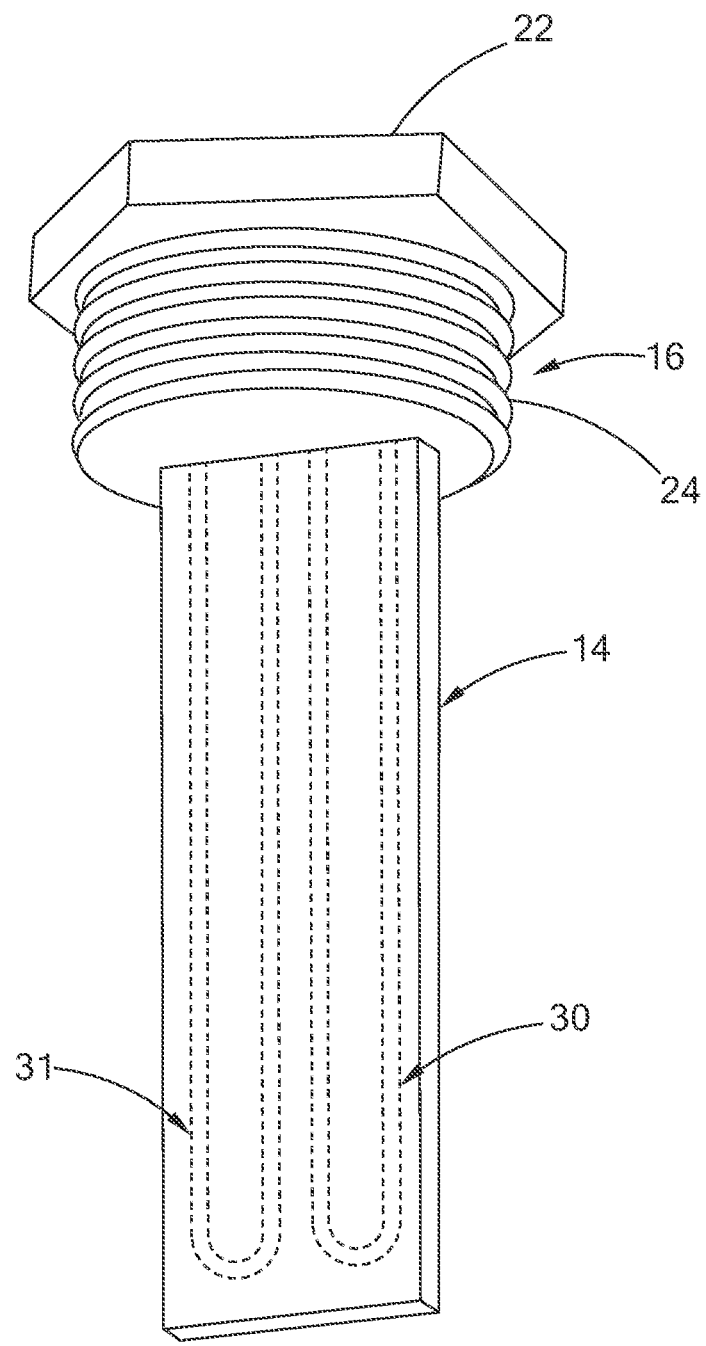
FIG. 2 is a partial perspective view of the apparatus of FIG. 1.
Figure 3:
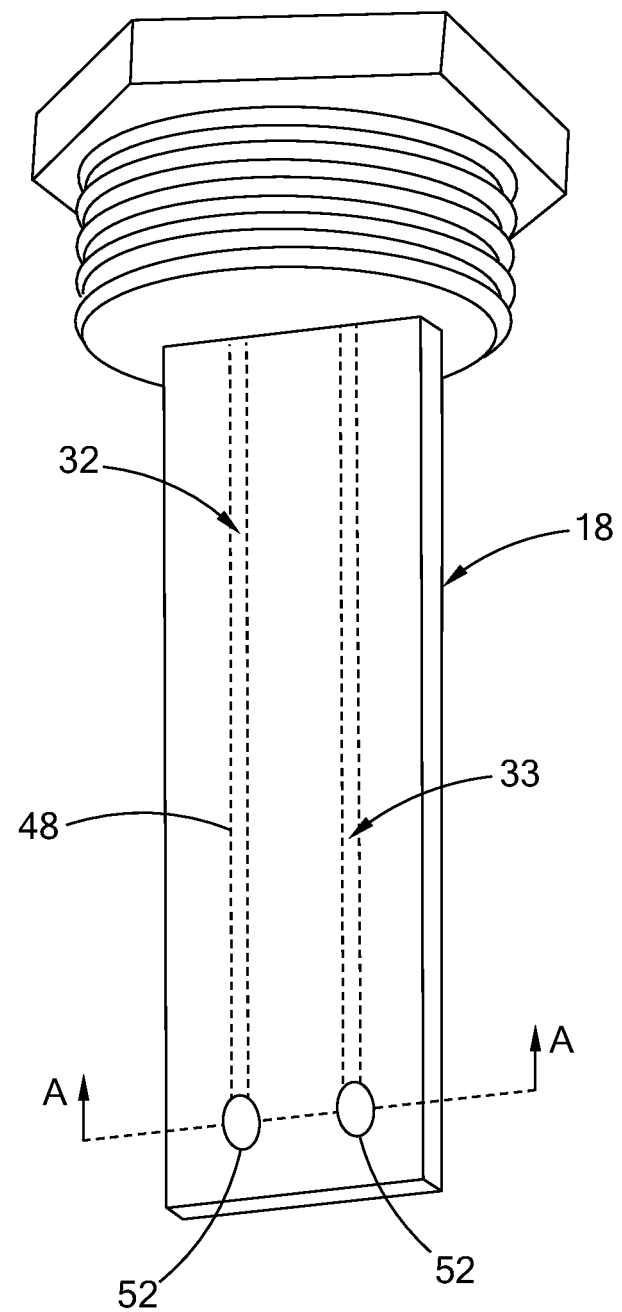
FIG. 3 is another partial perspective view of the apparatus of FIG. 1.

Referring to FIGS. 2 and 3, the probe section 18 includes a layered heater 30 and a fluid sensor 32. The layered heater 30 may be energized to heat the urea solution when the temperature of the urea solution is below a threshold temperature to ensure that the urea solution does not freeze, or to melt any accumulated ice particles. Likewise, the temperature of the urea solution can be controlled to be below a predetermined threshold in order to avoid degradation of the urea solution. As such, the layered heater 30 in one form can be designed to provide a Peltier effect for cooling. Additionally, in one form, the layered heater 30 is used as a temperature sensor to detect the temperature of the urea solution. Therefore, the layered heater 30 functions as both a heating element and a temperature sensor in one form of the present disclosure. Such a layered heater is described in greater detail in U.S. Pat. No. 7,196,295, which is commonly assigned with the present application and the contents of which are incorporated herein by reference in their entirety.

Figure 4:
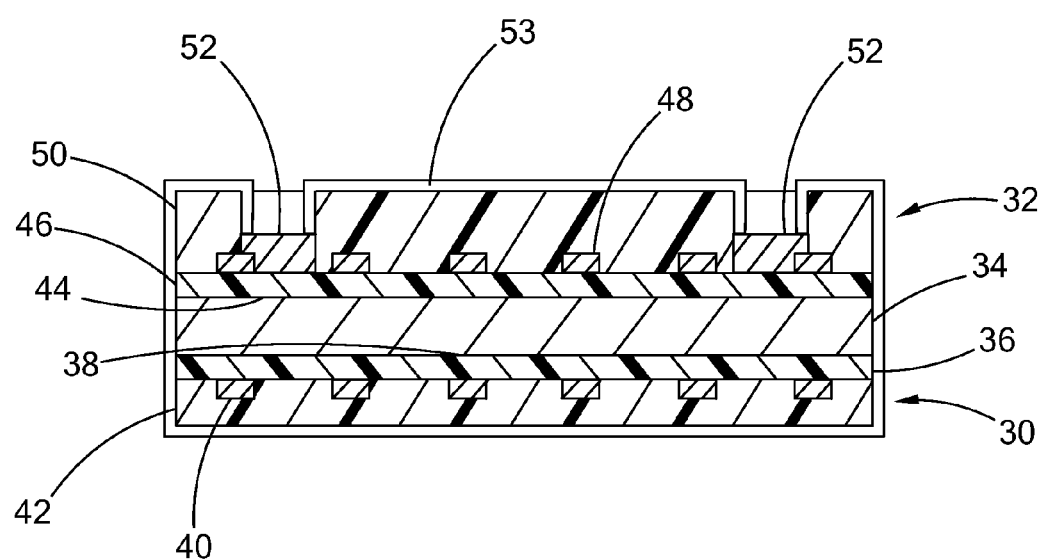
FIG. 4 is a cross-sectional view of the apparatus, taken along line A-A of FIG. 3.

Referring to FIG. 4, the probe section 18 includes a substrate 34 on which the layered heater 30 and the fluid sensor 32 are formed. The layered heater 30 may include a first dielectric layer 36 on a first surface 38 of the substrate 34, a resistive layer 40 on the first dielectric layer 36, and a second dielectric layer 42 on the resistive layer 40. The fluid sensor 32 includes a first dielectric layer 46 on a second surface 44 of the substrate 34, a conductive layer 48 on the first dielectric layer 46, and a second dielectric layer 50 on the conductive layer 48. A pair of conductive pads 52 are formed at the ends of the conductive layer 48 and not covered by the second dielectric layer 50. The functional layers (i.e., the dielectric layers 36, 42, 46, 50, the resistive layer 40, and the conductive layer 48) of the layered heater 30 and the fluid sensor 32 are formed by layered processes, such as thick film, thin film, thermal spray, plasma spray and sol-gel. Thick film processes may include, by way of example, screen printing, spraying, rolling, and transfer printing, among others. Thin film processes may include, by way of example, ion plating, sputtering, chemical vapor deposition (CVD), and physical vapor deposition (PVD), among others. Thermal spray process may include, by way of example, flame spraying, plasma spraying, wire arc spraying, and HVOF (High Velocity Oxygen Fuel), among others. Sol-gel processes may include, by way of example, dipping, spinning, or painting, among others. Thus, as used herein, the term "layered heater" should be construed to include heaters that comprise at least one functional layer (e.g., resistive layer 40 only, resistive layer 40 and dielectric layer 36/42 among others), wherein the layer is formed through application or accumulation of a material to a substrate or another layer using processes associated with thick film, thin film, thermal spraying, or sol-gel, among others. These processes are also referred to as "layered processes" or "layered heater processes."

As shown in FIGS. 2 and 3, the layered heater 30 includes a heating circuit 31, and the fluid sensor 32 includes a sensing circuit 33. The specific pattern of the heating circuit 31 and/or the sensing circuit 33 may be formed using stenciling, laser trimming, etching, or machining, among other methods associated with layered processes. For example, the laser trimming as set forth in U.S. Pat. No. 7,361,869, which is commonly assigned with the present application and the contents of which are incorporated herein by reference in their entirety, may be employed while remaining within the scope of the present disclosure.

As further shown in FIG. 4, a protective coating 53, such as a metal material, may be applied on the second dielectric layers 42 and 50 of the layered heater 30 and the fluid sensor 32 to protect the heater 30 and fluid sensor 32 from corrosion by the urea solution or other environmental damage.

Figure 5:
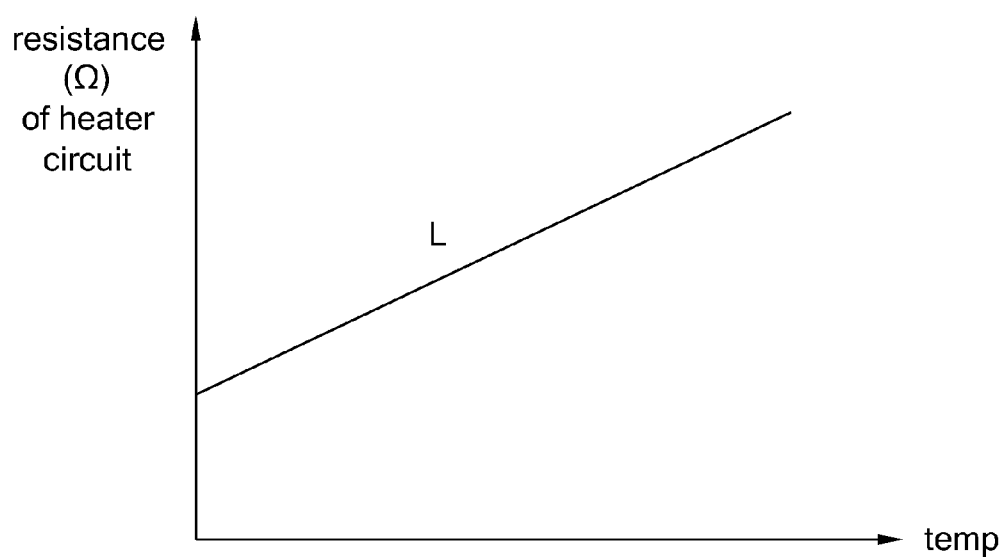
FIG. 5 is a graph showing a relationship between resistance of a heating circuit and the temperature.

Referring to FIG. 5, the resistive layer 40 of the layered heater 30 forms the heating circuit 31 and includes a material having a relatively high temperature coefficient of resistance (TCR), whether positive or negative. When the heating circuit 31 includes a material having a positive temperature coefficient, the resistance of the heating circuit 31 increases with the temperature of the heating circuit. The resistance at any temperature t (° C.) may be described as $R_0(1+\alpha t)$, wherein $R_0$ is the resistance at a reference temperature (often 0° C.) and $\alpha$ is the temperature coefficient of resistance (TCR). As shown, the resistance of the heating circuit 31 is a function of the temperature of the heating circuit 31, and the slope of the line L depends on material of the heating circuit 31.

Figure 6:
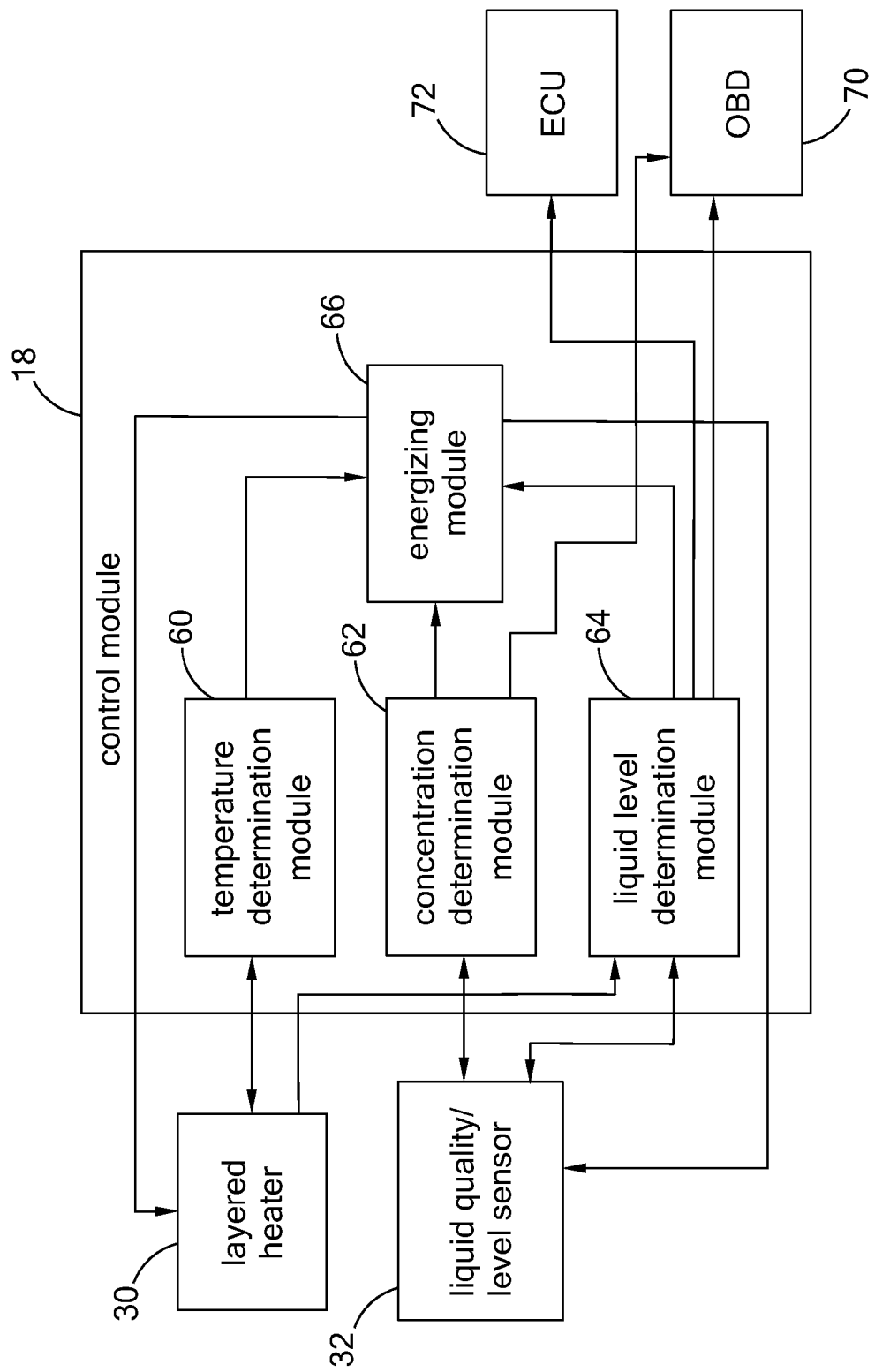
FIG. 6 is a schematic view of a control module of the apparatus.

Referring to FIG. 6, the control module 18 includes a temperature determination module 60, a concentration determination module 62, a fluid level determination module 64, and an energizing module 66. The temperature determination module 60 is in communication with the layered heater 30 and may include a two-wire controller. The two-wire controller determines temperature of the layered heater by measuring the resistance of the resistive layer 40 and controls heater temperature through the energizing module 66. The voltage applied to and the current passing through the layered heater 30 is measured using the two-wire controller, and a resistance is calculated based on Ohm's law. Additionally, a high-temperature limit switch (not shown) may also be employed while remaining within the scope of the present disclosure.

To determine and control the temperature of the urea solution, the layered heater 30 may be energized by the energizing module 66 for a predetermined period. The resistive layer 40 of the layered heater 30 heats up and heats the surrounding urea solution. The resistance of the resistive layer 40 changes as a function of temperature. By determining the change of resistance of the resistive layer 40, the temperature of the resistive layer 40 and the urea solution can be determined. A layered heater including a resistive layer as both a heater element and temperature sensor and a two-wire controller for controlling same have been described in U.S. Pat. No. 7,196,295, titled "Two-Wire Layered Heater System," assigned to the present assignee and the disclosure of which is incorporated herein by reference in its entirety.

Figure 7:
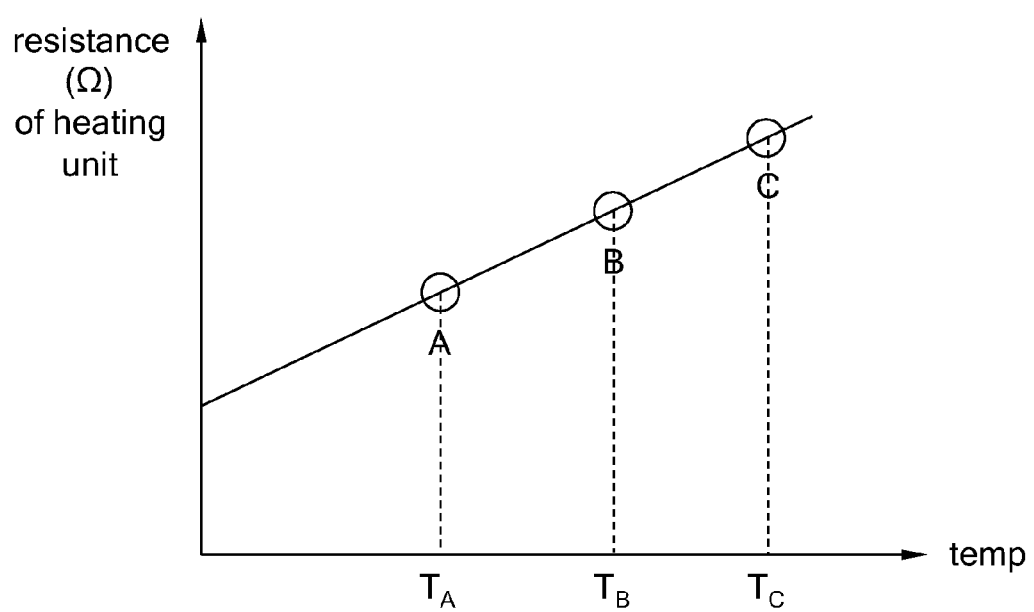
FIG. 7 is another graph showing the relationship between the resistance of a heating circuit and temperature.

Referring to FIG. 7, the layered heater 30 may also be used to determine whether the level of the urea solution is below a threshold level. As shown and previously described, the resistance of the heating circuit 31 increases with the temperature of the heating circuit 31 and consequently the temperature of the urea solution when the resistive layer 40 includes a material having a positive temperature coefficient. As shown, point A indicates an initial temperature $T_A$ and resistance $R_A$ of the heating circuit 31 when the layered heater 30 is not energized. The layered heater 30 may be energized for a predetermined period $\Delta t$ to increase the temperature and resistance of the heating circuit 31. Point B indicates a final temperature $T_B$ and a final resistance of the heating circuit 31 after the heater circuit 31 is energized when a predetermined amount of the urea solution is present in the tank. The temperature and the resistance of the heating circuit 31 increase at a higher rate when less urea solution is contained. The more the urea solution in the tank 12, the closer point B is to point A. The less the urea solution in the tank 12, the farther point B is away from point A given the same amount of energy in. When the final temperature and resistance exceeds an upper threshold (for example, the temperature and resistance indicated by point C), the fluid level determination module 64 may determine that the liquid level of the urea solution is below a lower threshold. The fluid level determination module 64 may send a signal to an alarm or an On Board Diagnostic (OBD) system 70 to alert the driver. Furthermore, the system may be designed/programmed to provide periodic testing of the urea solution level, among other characteristics, such as during start-up and intervals during use. Additionally, the fluid level determination module 64 may send a signal to the engine control unit (ECU) 72 to control the engine to run at a lower speed to reduce emissions. The system may further be configured to communicate fluid characteristics to status gauges and other devices for controlling an engine, device, or process. Such configurations should be construed as falling within the scope of the present disclosure.

Figure 8A:
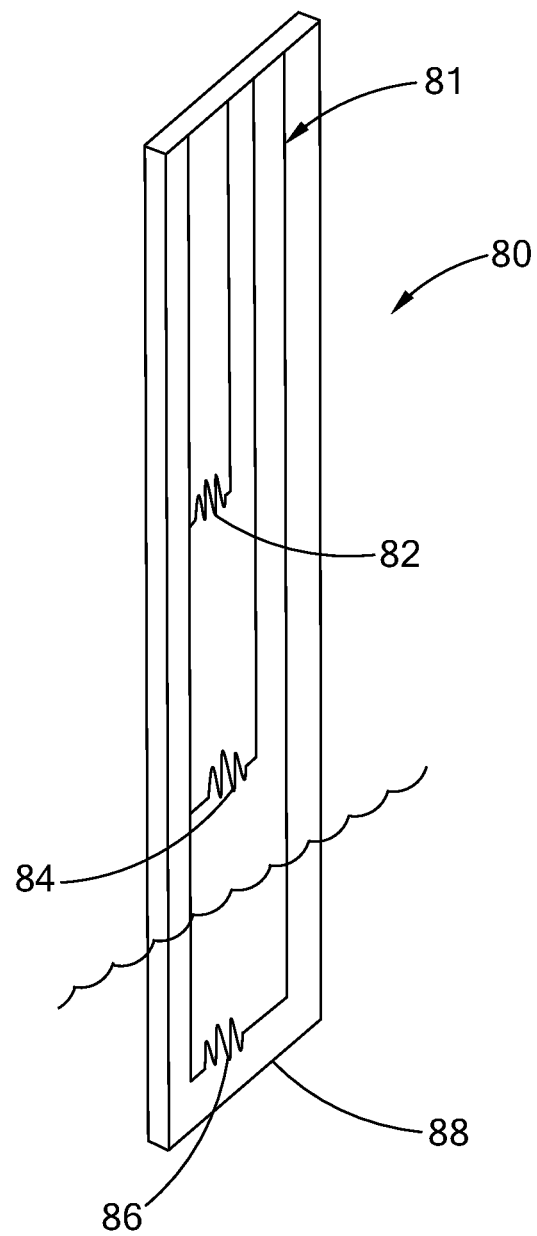
FIG. 8A is a schematic view of an alternative form of a heating circuit of a layered heater.

Referring to FIG. 8A, an alternative form of the layered heater 80 is configured to more precisely determine the liquid level of the urea solution. As shown, the layered heater 80 includes a heating circuit 81 including a plurality of resistors 82, 84, 86 which are arranged at different points along the length of the probe section 14, indicating different elevations of the tank 12. For example, the first resistor 82 may be provided at a middle point of the probe section 14. The second resistor 84 may be provided at a middle point between the first resistor 84 and a bottom edge 88 of the probe section 14. The third resistor 86 may be provided proximate the bottom edge 88 of the probe section 14. Therefore, the locations of the first resistor 82, the second resistor 84, the third sensor 86 correspond to a plurality of liquid levels, i.e., ½ full, ¼ full, and close to emptiness.

When the heating circuit 81 is energized, the temperature and resistance of the resistors 82, 84 and 86 increase if the resistors 82, 84 and 86 have a PTC (positive temperature coefficient) material. When the resistors 82, 84 and 86 include similar materials and are configured similarly, the temperature and the resistance of the resistors 82, 84 and 86 increase at the same rate under similar conditions. When one or two of the resistors 82, 84 and 86 are immersed in the urea solution, the resistors in the urea solution are heated at a lower rate. As a result, resistance of the resistors 82, 84 and 84 are not the same after the resistors are energized for the same amount of time. Therefore, the liquid level of the urea solution can be determined based on a comparison of the temperature change and a resistance change in these resistors 82, 84 and 86. It is understood that more resistors can be provided, for example, at ¾ full level and ⅛ full level, to more precisely determine the level of the urea solution. Furthermore, the value of each of the resistors may be modified to optimize individual signatures. In still another form, the control module 18 can multiplex between each of the resistors in order to determine the urea solution level.

Referring back to FIG. 3, the fluid sensor 32 includes a conductive layer 48 and a pair of conductive pads 52. A net electrical potential is established between the conducive pads 52. The conductive pads 52 are exposed to the urea solution to detect the electrical conductivity of the urea solution. The conductive pads 52 include a corrosion-resistant material (for example, stainless steel) to protect the conductive pads 52 from the urea solution, which may have a PH level as high as 10.

The fluid sensor 32 is in communication with the concentration determination module 62, the fluid level determination module 64 and the energizing module 66 of the control module 18. To detect the quality of the urea solution, an electrical potential may be applied to the conductive pads 52. Electrical current passes between the conductive pads 52 through the urea solution at a rate proportional to the electrical conductivity of the urea solution. When the urea is contaminated or diluted, the electrical conductivity deviates from the predetermined electrical conductivity. Therefore, the fluid sensor 32 may detect the concentration, contamination, or dilution of the urea solution based on electrical conductivity of the urea solution.

Additionally, the fluid sensor 32 may detect whether the fluid level is below a predetermined level. When the conductive pads 52 are located above the liquid level, no urea solution is present between the conductive pads 52 to establish electrical connection therebetween. Therefore, when no electrical connection between the conductive pads 52 is detected, the fluid level determination module 64 may determine that the fluid level is below the conductive pads 52 (or a predetermined level).

Figure 8B:
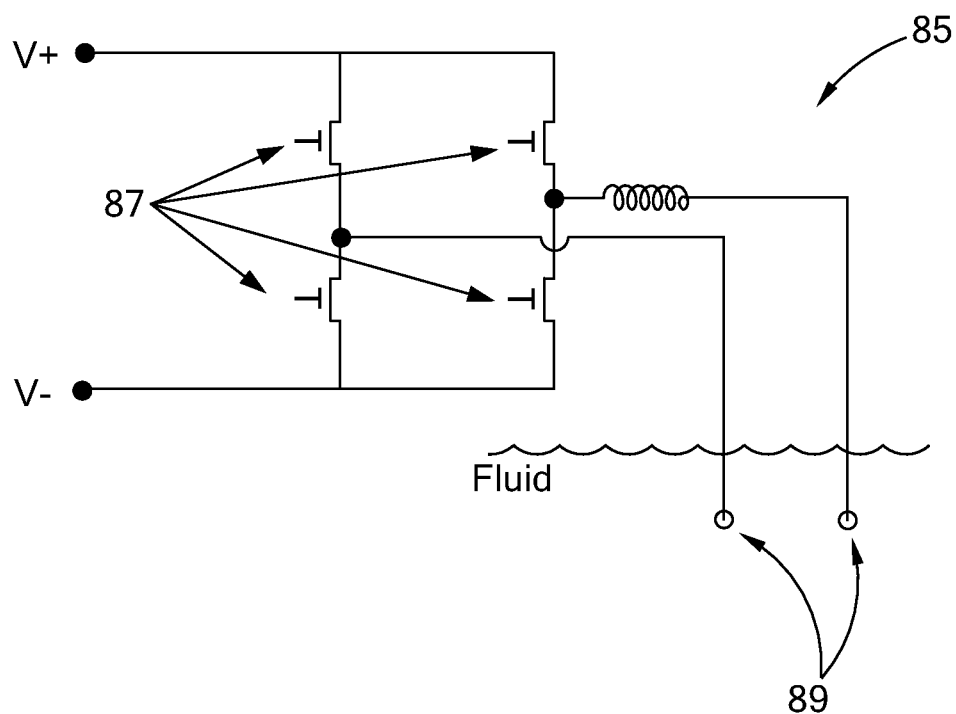
FIG. 8B is a schematic view of a circuit to determine characteristics of a fluid in accordance with the principles of the present disclosure.

As shown in FIG. 8B, an exemplary circuit that is able to determine characteristics of the fluid is illustrated and generally indicated by reference numeral 85. In this circuit 85, a set of four switches 87 are included and the polarity of the voltage is continually toggled with these switches 87 to fluctuate the electric field between the elements 89 disposed within the fluid. Accordingly, various characteristics of the fluid can be determined based on the differences between the elements 89, which may be, for example capacitance or dielectric based, as set forth herein.

Figure 9A:
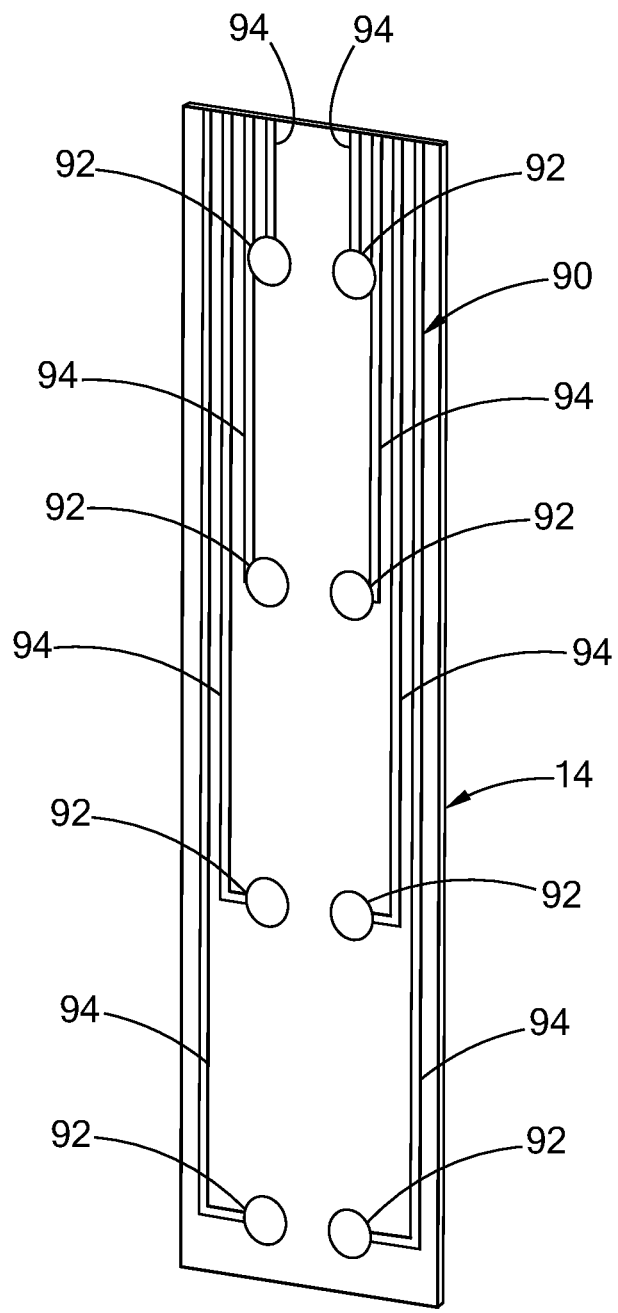
FIG. 9A is a schematic view of an alternative form of a sensing circuit of a fluid sensor according to the present disclosure.

Referring to FIG. 9A, an alternative form of a fluid sensor 90 may be used to more precisely detect the liquid level of the urea solution. As shown, the fluid sensor 90 includes a plurality of conductive pads 92 and a plurality of electrical buses 94 connected to the conductive pads 92. The conductive pads 92 are arranged in pair at different points along the length of the probe section 14 corresponding to different elevation of the tank 12. The conductive pads 92 immersed in the urea solution are electrically connected by the urea solution, whereas the conductive pads 92 above the level of the urea solution are not electrically connected. Therefore, the fluid level may be more precisely determined based on whether electrical connection is established between the conductive pads 92 at different levels. In still another refinement, the fluid itself could be an actual heater circuit, where an electrical charge is applied using electrodes dispersed within the fluid. For example, the current flowing between the conductive pads 92 would be provided at a sufficient level to create Joule heating of the fluid.

Figure 9C:
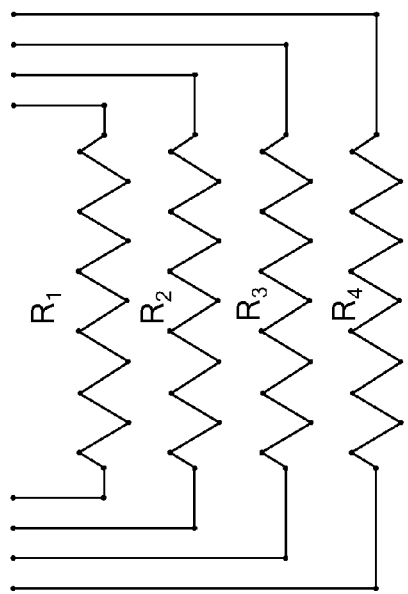
FIG. 9C is a schematic view of yet another form of a sensing circuit of a fluid sensor according to the present disclosure.
Figure 9B:
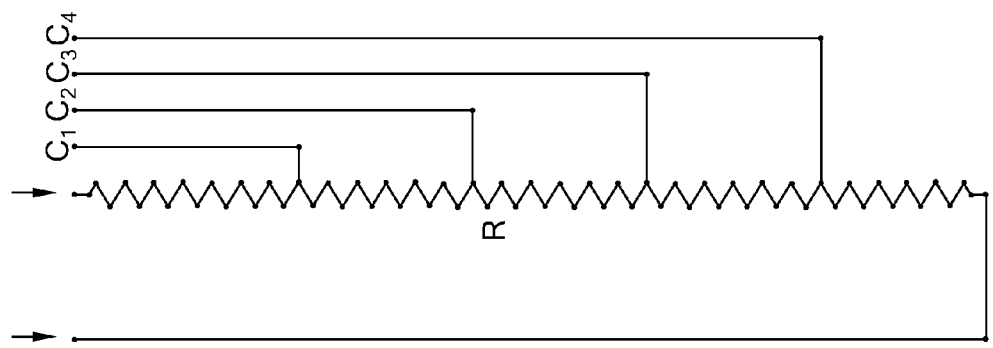
FIG. 9B is a schematic view of still another form of a sensing circuit of a fluid sensor according to the present disclosure.

As further shown in FIGS. 9B and 9C, determining the characteristics of the fluid using the pads can be combined with/into the heater circuit. When the pads (illustrated as resistors "R" in FIGS. 9B and 9C) are integrated within the actual heater circuit, the control module 18 uses multiplexing to read various combinations of loads on the resistors R to determine the fluid characteristics. For example, in FIG. 9B, the fluid level can be determined by comparing the resistance of the various nodes (N1, N2, N3, and N4). It should be understood that any number of circuits may be employed and the illustration of four (4) circuits is merely exemplary. As another example, as shown in FIG. 9C, electromagnetic fields generated by parallel circuits are employed to determine electrical properties of the fluid, thereby determining, for example, whether or not the fluid has been contaminated. These and other circuit variations constructed in accordance with the teachings herein shall be construed to be within the scope of the present disclosure.

Figure 9D:
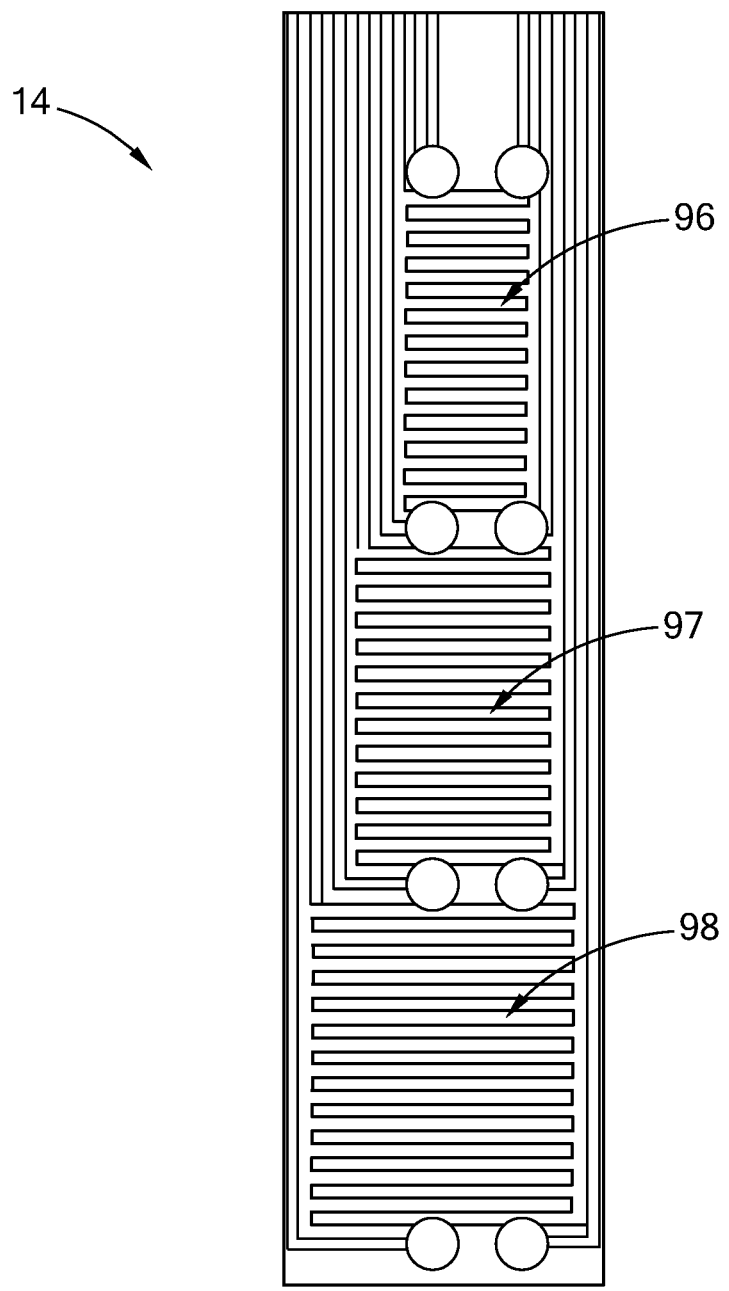
FIG. 9D is a schematic view of another form of a sensing circuit of a fluid sensor according to the present disclosure.

As shown in FIG. 9D, individual heater circuits 96, 97, and 98 are disposed along the probe section 14. In operation, as the fluid level decreases, the individual heater circuits are turned off in order to improve efficiency of the fluid heater.

Figure 10:
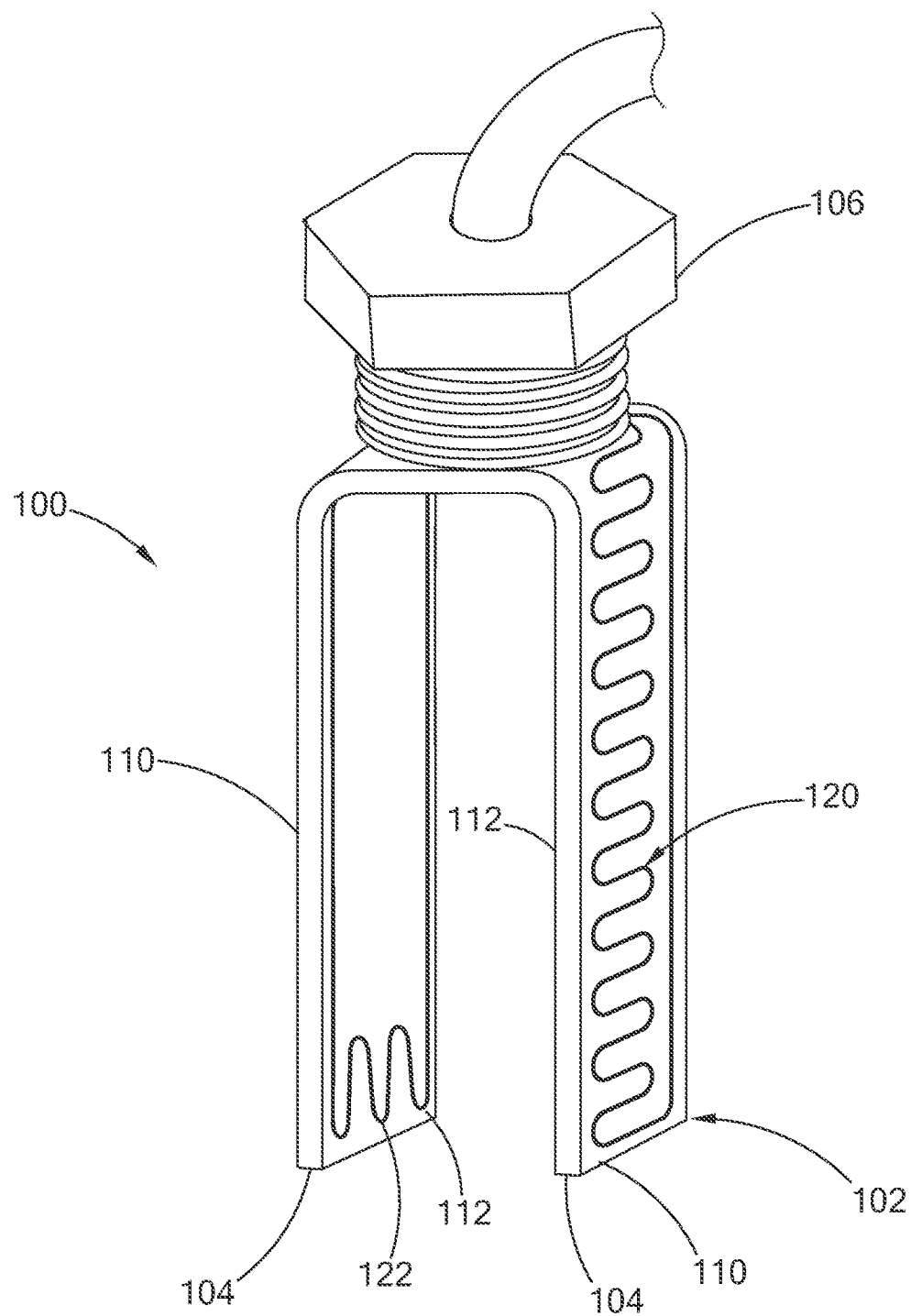
FIG. 10 is a perspective view of an alternative form of an apparatus in accordance with the principles of the present disclosure.

Referring to FIG. 10, an alternative form of an apparatus 100 is shown to be similar to the apparatus 10 except for the probe section 102. More specifically, the probe section 102 includes a plurality of legs 104 extending from the mounting section 106. While two legs are shown, it is understood that the probe section 102 may have any number (including one) of legs. The legs 104 each have a flat plate configuration and include an outer surface 110 and an inner surface 112. The inner surfaces 112 of the legs 104 face each other. The apparatus 100 includes a layered heater 120 proximate the outer surfaces 110 and a fluid sensor 122 proximate the inner surface 112. Similarly, the layered heater 120 and the fluid sensor 122 are formed on a substrate of the probe section 102 by layered processes.

Figure 11:
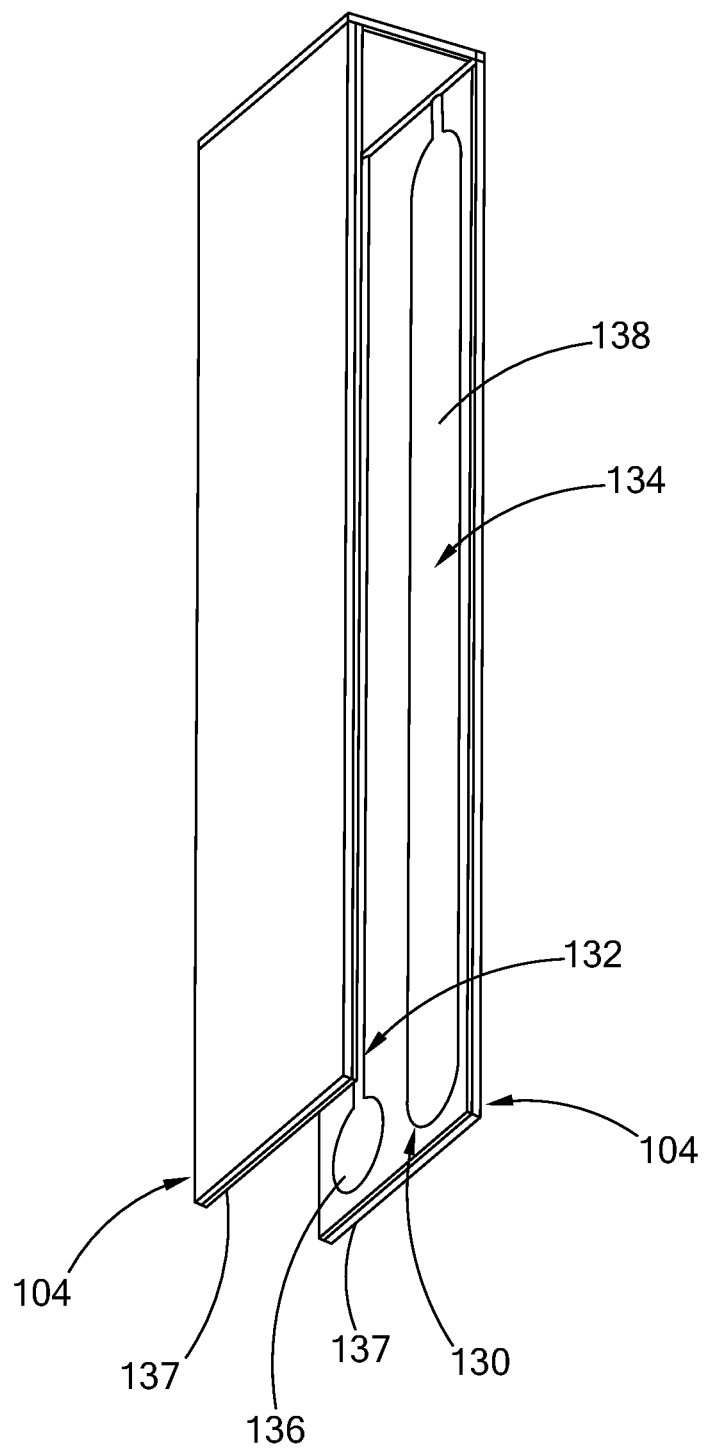
FIG. 11 is a schematic view of an alternative form of a sensing circuit of a fluid sensor.

Referring to FIG. 11, an alternative form of a fluid sensor 130 may be provided proximate the inner surfaces of the legs 104. The liquid quality/level sensor 130 includes a first capacitive sensing element 132 and a second capacitive sensing element 134. The first capacitive sensing element 132 includes a pair of conductive pads 136 (only one is shown in FIG. 11) with one on each leg 104. The pair of conductive pads 136 are provided near a bottom edge 137 of the probe section 14 (i.e., the bottom of the tank 12) to measure the dielectric constant of the urea solution. (Dielectric constant refers to the ability of a material to be polarized by an applied electric field)_. An electrical potential may be applied to the conductive pads 136. The magnitude of electrical current may be affected by materials in the space between the conductive pads 136. The urea solution with different concentration (having different electrical resistance) will have a different effect on the electrical current. Therefore, the concentration of the urea solution may be determined based on the dielectric constant of the urea solution. Moreover, different liquids have different dielectric constants. The type of liquids (e.g., diesel fuel, water, urea) present in the tank may also be determined based on the dielectric constant.

Additionally, because air is a poor electrical conductor, it can be determined that the liquid level may be below the conductive pads 136.

The second capacitive sensing element 134 include a pair of electrodes 138 with one on each leg 104 and extending along the length of the probe section 14 (i.e., the elevation of the tank 12) to measure the fluid level based on capacitance between the electrodes 138. An electromagnetic field may be applied to the electrodes 138. The magnitude of the electromagnetic field is affected by materials in the space between the electrodes 138. Materials with high dielectric constant (such as air) have a greater effect on the electromagnetic field and may change the capacitance between the electrodes 138. Therefore, the capacitance between the electrodes 138 provides an indication of the fluid level.

Figure 12A:
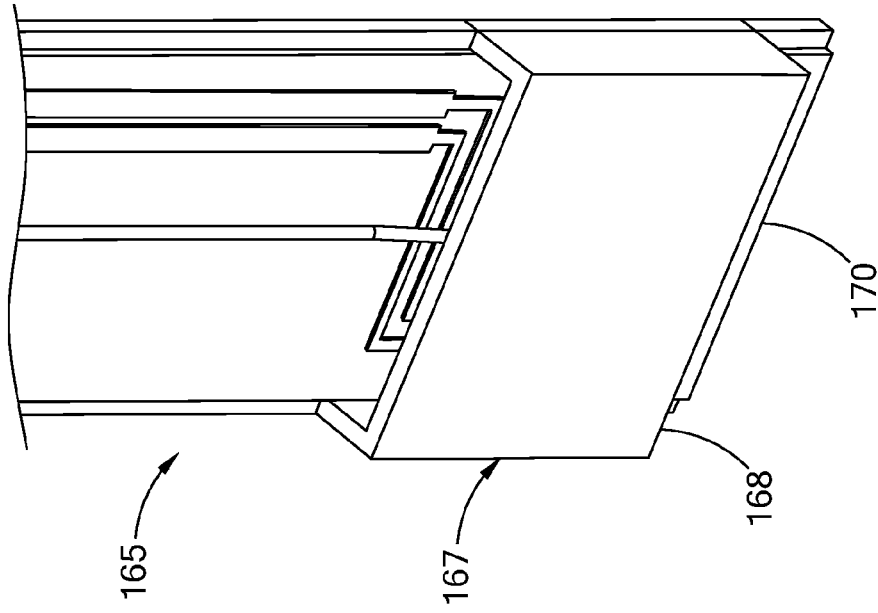
FIG. 12A is a perspective view of an alternative form of a probe section of an apparatus.

Referring to FIG. 12A, an alternative form of a probe section 150 includes a rectangular tubular body 151 defining an upper open end 152, a lower open end 154, and a hollow space 156 therebetween. The upper open end 152 and the lower open end 154 allow the urea solution to enter the hollow space 156. Lateral fluid flow is restricted. The probe section 150 includes a layered heater (not shown) in any form as described previously in connection with FIGS. 2, 4, and 8, and a fluid sensor 162. The fluid sensor 162 may include a heating element 164 and a thermocouple 166 provided proximate a middle portion of the rectangular tubular body 151 for measuring the temperature of the urea solution contained in rectangular tubular body 151.

In one form, the concentration of the urea solution is determined based on specific heat of the urea solution present in the hollow space 156 of the probe section 150. When the heating element 164 is energized (for example, by applying a voltage) for a predetermined period, the heating element 164 generates heat to heat the urea solution enclosed in the rectangular tubular body 151. The increased temperature is a function of the specific heat of the urea solution and the length of the heater immersed in the urea solution. When the specific heat deviates from a predetermined specific heat, it can be determined that the fluid is contaminated or diluted. The specific heat of a fluid is calculated by measuring the temperature change caused by a known quantity of heat.

It is understood that the heating element 164 can be eliminated and the layered heater that is used to heat urea solution outside the rectangular tubular body 151 may be energized to provide the required heat for determining the specific heat.

Figure 12B:
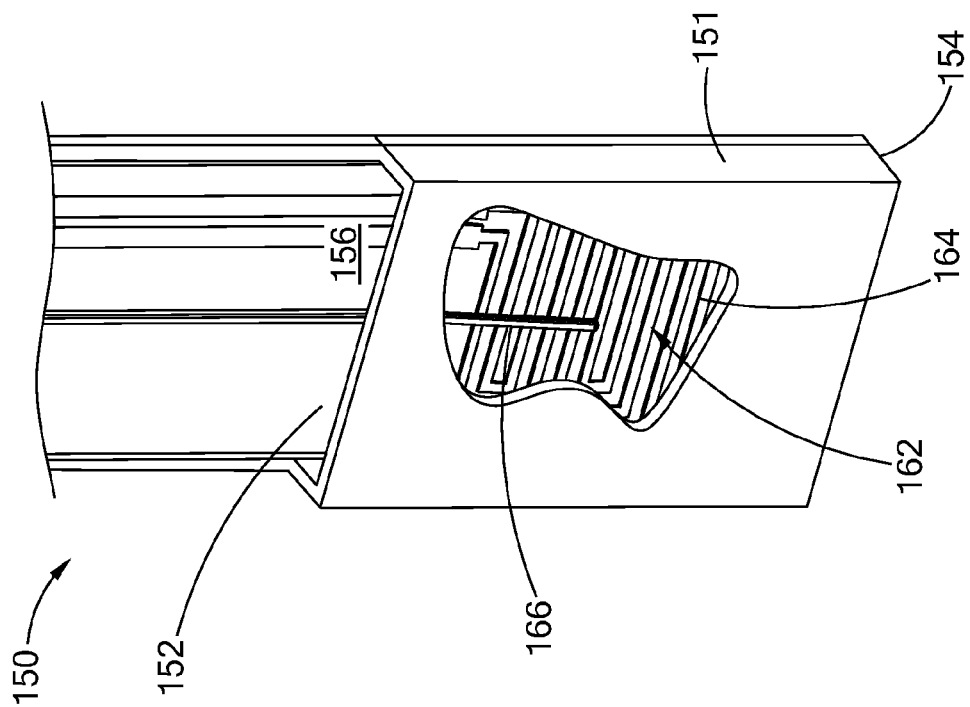
FIG. 12B is a perspective view of another alternative form of a probe section.

Referring to FIG. 12B, an alternative form of a probe section 165 is shown to be similar to that of FIG. 12A, differing in that rectangular tubular body 167 is smaller and the lower open end 168 is spaced apart from the bottom edge 170 of the probe section 165.

In summary, the characteristics of the urea solution contained in the tank 12 (for example, type, concentration, and whether the urea solution is contaminated or diluted) may be determined by a fluid sensor based on electrical conductivity, dielectric constant, and specific heat of the urea solution. Additionally, the fluid sensor may also be used to detect the fluid level if proper arrangement of the sensing circuit and calculation is made. For example, the conductive pads of the fluid sensor may be used to detect the fluid level if arranged at different points of interests corresponding to different fluid levels.

Figure 13:
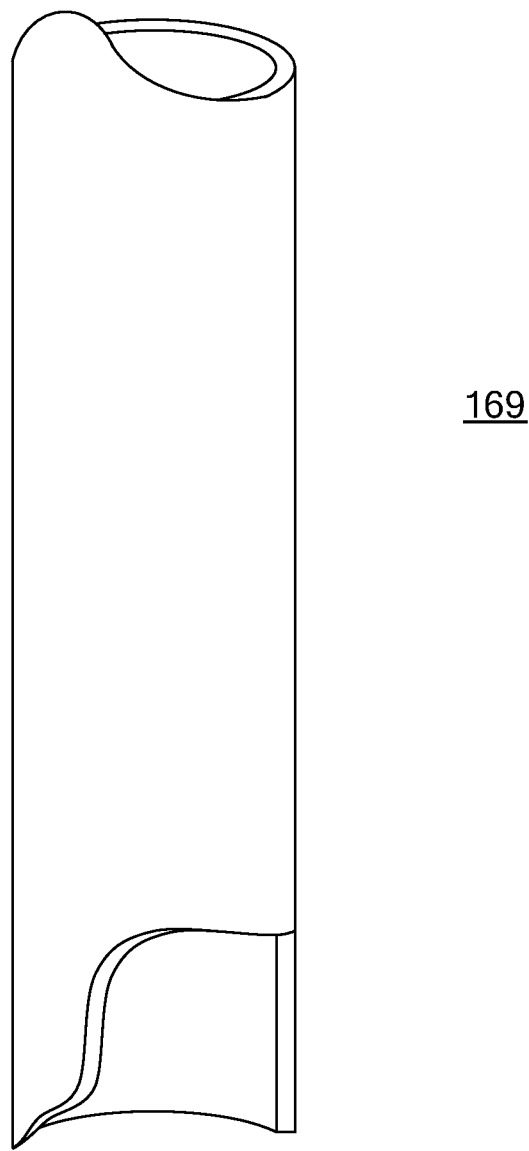
FIG. 13 is a perspective view of a probe section of an apparatus in accordance with principles of the present disclosure.

Referring to FIG. 13, an alternative form of the probe section 169 is shown to have a cylindrical tubular configuration, instead of a flat plate configuration. The heater circuit may be provided proximate an outer cylindrical surface. The liquid quality/level sensing circuit based on the specific heat may be provided proximate an inner cylindrical surface.

Figure 14:
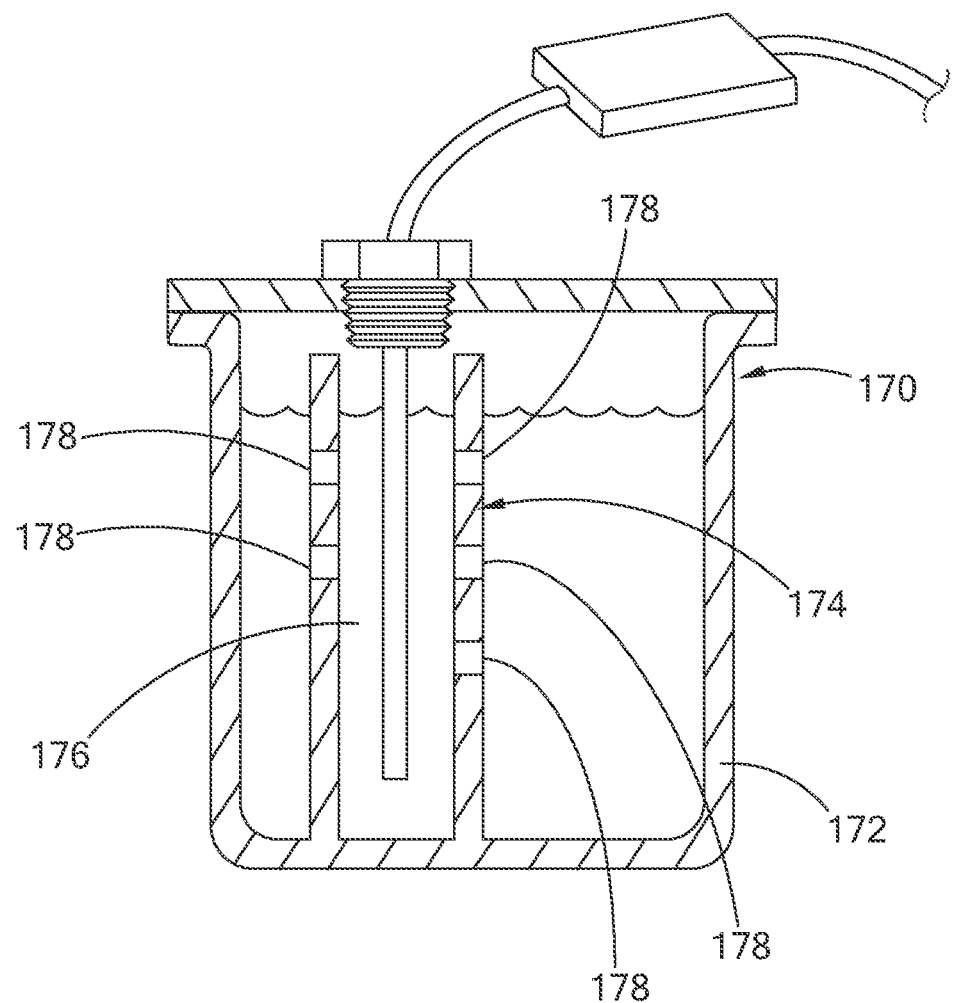
FIG. 14 is a perspective view of an alternative form of a tank for use with an apparatus in accordance with the present disclosure.

Referring to FIG. 14, an alternative form of a tank 170 for use with the sensing apparatus in accordance with the principles of the present disclosure is shown to include a tank body 172 and a tubular wall 174. The tubular wall 174 defines a space 176 for receiving the probe section 14 of the apparatus 10. The tubular wall 174 defines a plurality of apertures 178 to allow for fluid communication inside and outside the tubular wall 174. The tubular wall 174 is provided to prevent fluid "sloshing" in the tank 170 when the vehicle travels. Fluid "sloshing" may cause unpredictable fluid flow and fluid mixing. The tubular wall 172 isolates the sample of fluid from the rest of the tank 170, minimizes instantaneous sloshing of fluid, helps reduce error in the liquid level calculation, and also provides a small volume where a first portion of thawed urea can be sampled.

Figure 15:
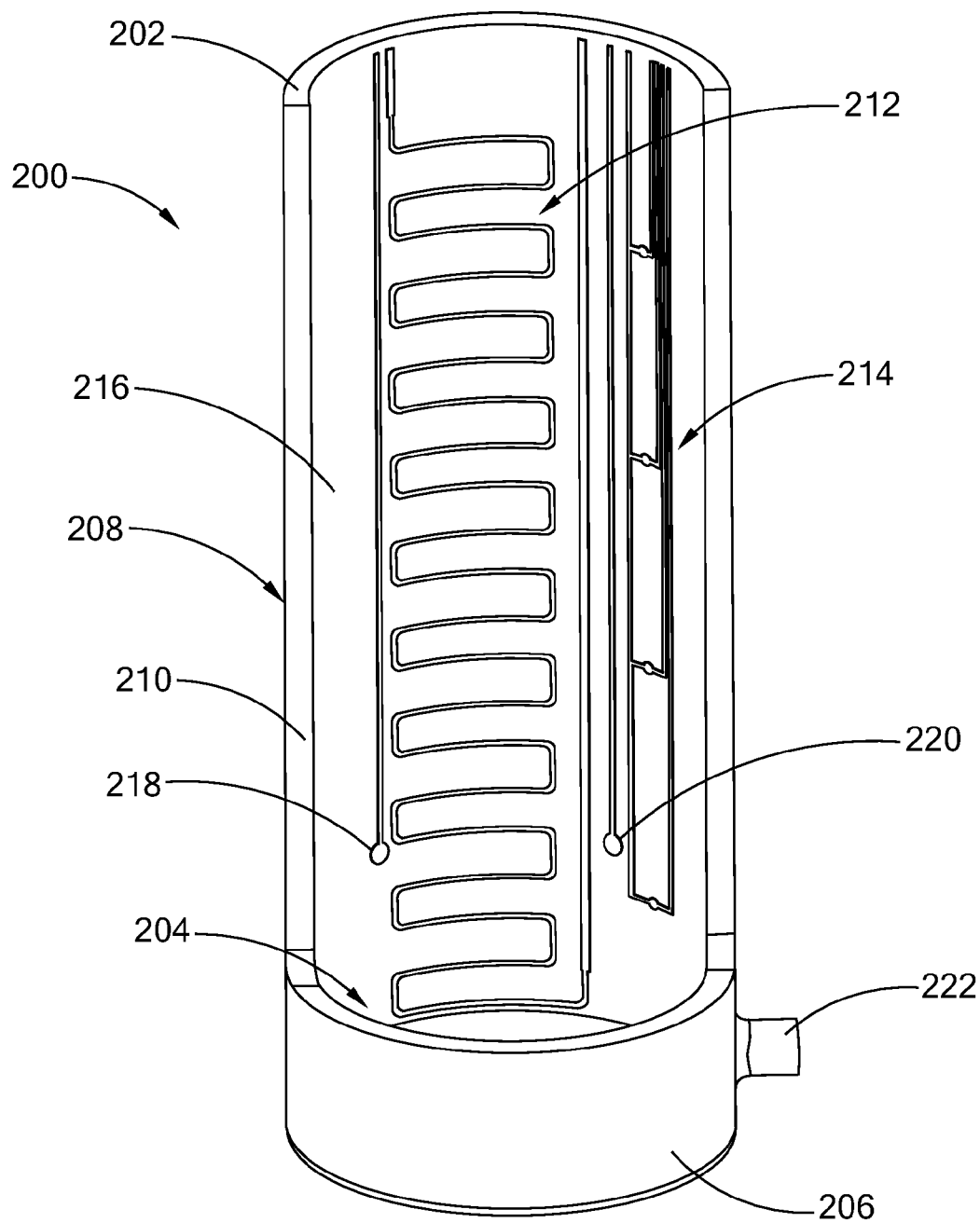
FIG. 15 is a perspective view of another combination probe constructed in accordance with the present disclosure.

Referring now to FIG. 15, another form of a probe constructed in accordance with the principles of the present disclosure is illustrated and generally indicated by reference numeral 200. The probe 200 includes a tubular body 202 having a lower reservoir 204 formed by a lower wall enclosure 206, and the remainder of the probe 200 is exposed to the fluid by the cutout 208. Although the cutout 208 is shown as approximately a 180° cut in the sidewall 210 of the tubular body 202, it should be understood that alternate size cutouts may be employed while remaining within the scope of the present disclosure. For example, the cutout 208 may be a relatively small slit sized to allow the fluid to enter the tubular body 202 while further reducing "slosh" associated with the fluid movement. Alternately, a plurality of perforations (not shown) may be provided through the sidewall 210, rather than a single, discrete opening.

As further shown, a heater circuit 212 and a sensor circuit 214 are disposed along an inner wall 216 of the tubular body 202. These circuits operate as previously set forth in greater detail above and thus will not be described further for sake of clarity. Additionally, other sensors may be disposed along the inner wall 216, such as, by way of example, a quality sensor 218 (which may be capacitance or dielectric based, as set forth above), and a level sensor 220. Accordingly, any number of sensors and/or circuits may be disposed along the inner wall 216 of the tubular body 202 while remaining within the scope of the present disclosure. It should also be understood that one or more of the sensors and/or circuits may be disposed along an outer wall of the tubular body 202 while remaining within the scope of the present disclosure.

Generally, the lower reservoir 204 is sized to accommodate or capture fluid as it melts from contact with the heater circuit 212, thus reducing the amount of current to only that required to meet fluid flow demands and not melt frozen fluid throughout the entire tank (not shown). In one form, the lower reservoir 204 would be disposed within a recess in the tank to reduce the amount of residual fluid, and a filter element (not shown) could be disposed proximate the reservoir outlet 222, if necessary.

Although not shown, the concept of including circuits and elements on an inner wall of the tubular body 202 may be realized by incorporating such circuits and elements on a flexible substrate, such as a polyimide sheet, which is then secured to the inner wall of the tubular body 202. It should also be understood that the probe 200 may take on shapes other than tubular, such as rectangular, oval, or polygonal, among others. Furthermore, the various circuits and elements illustrated and described herein may be integrated directed into the inner wall of the tank such that a separate/discrete probe is not required. Such variations shall be construed as falling within the scope of the present disclosure.

The apparatus in accordance with the principles of the present disclosure advantageously provides a plurality of sensors and a heater integrated in one unit. The heating circuit of the heater and the sensing circuits of the sensors are formed on a substrate by layered processes, resulting in a compact structure. Moreover, a control module that includes control circuits and algorithms are in communication with the plurality of sensing circuits and the heating circuit for controlling the heating and sensing circuits and determining characteristics of the urea solution based on signals from the heating and sensing circuits. The control module may also be in communication with an on-board diagnostic (OBD) system or Engine Control Unit (ECU), using bus communication protocols such as CAN J1939 or LIN, among others, to communicate the quality, temperature, and/or physical state of the urea solution. Based on fluid level, temperature, and physical state, the ECU can control engine speed and power output as required for emission standards compliance. The output of the control module can also be used to optimize system performance and NOx reduction by communicating when the liquid level is low or signal the ECU when frozen fluid has been thawed and is available. Therefore, the quality of the urea can be verified real time for diesel engines to ensure effective NOx reduction and emission standards compliance.

While the present disclosure has been discussed above with particular attention to the urea solution, it is to be understood that the teachings disclosed herein, including its various forms, is not limited to such an application and can be employed to determine characteristics of other fluids.

When describing elements or features and/or forms of the present disclosure, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary forms and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that each process or step can be repeated more than once and that additional or alternative processes or steps may be employed and still be within the scope of the present disclosure.

What is claimed is:

1. An apparatus for determining and controlling characteristics of a fluid comprising:
   a substrate;
   a heating circuit applied on the substrate for controlling characteristics of the fluid; and
   a sensing circuit distinct from the heating circuit applied on the substrate for determining characteristics of the fluid;
   wherein the heating circuit is applied on the substrate by a layered process comprising a first dielectric layer, a resistive layer and a second dielectric layer, and
   wherein the sensing circuit is applied on the substrate by a layered process comprising a first dielectric layer, a conductive layer and a second dielectric layer.

2. The apparatus according to claim 1 wherein the layered process is selected from a group consisting of thick film, thin film, thermal spray, plasma spray, and sol-gel.

3. The apparatus according to claim 1 wherein the heating circuit has resistance which changes with temperature and is used for both heating and sensing temperature of the fluid.

4. The apparatus according to claim 1, wherein the fluid is a urea solution.

5. An apparatus for determining and controlling characteristics of a fluid comprising:
   a substrate;
   a heating circuit applied on the substrate for controlling characteristics of the fluid; and
   a sensing circuit applied on the substrate for determining characteristics of the fluid:
   wherein the heating circuit and the sensing circuit are applied on the substrate by a layered process and wherein the sensing circuit includes a pair of conductive pads for detecting one of electrical conductivity and dielectric constant of the fluid.

6. The apparatus according to claim 5 further comprising a control module that determines at least one of type, concentration, temperature, and level of the fluid based on output signals from at least one of the sensing circuit and the heating circuit.

7. The apparatus according to claim 6 wherein the control module determines concentration of the fluid based on the one of the electrical conductivity and the dielectric constant.

8. The apparatus according to claim 6 wherein the sensing circuit includes a plurality of conductive pads arranged in pair at a plurality of locations corresponding to a plurality of liquid levels.

9. The apparatus according to claim 8 wherein the control module determines the liquid level of the liquid solution based on the one of electrical conductivity and dielectric constant of the fluid and the locations of the conductive pads.

10. The apparatus according to claim 6 wherein the control module determines that the fluid level is below a threshold when resistance of the heating circuit exceeds a predetermined value after the heating circuit is energized for a predetermined period.

11. The apparatus according to claim 6 wherein the heating circuit includes a plurality of resistors corresponding to a plurality of levels.

12. The apparatus according to claim 11 wherein the control module determines the level of the fluid based a comparison of the resistance of the plurality of resistors after the plurality of resistors are energized for a predetermined period.

13. The apparatus according to claim 6 wherein the control module determines concentration of the fluid based on specific heat of the fluid.

14. The apparatus according to claim 5, wherein the sensing circuit comprises a first dielectric layer, a conductive layer and a second dielectric layer and the pair of conductive pads are expose through the second dielectric layer.

15. An apparatus for determining and controlling characteristics of a fluid comprising:
   a probe section;
   a layered heating circuit comprising a plurality of resistors arranged at a plurality of locations corresponding to a plurality of fluid levels formed on the probe section and having resistance that changes with temperature; and
   a control module in communication with the heating circuit,
   wherein the control module determines at least one of type, concentration, temperature and level of the fluid based on a change of the resistance of the layered heating circuit.

16. The apparatus according to claim 15 wherein the control module determines concentration and temperature of the fluid based on the change of resistance of the heating circuit after the heating circuit is energized for a predetermined period.

17. The apparatus according to claim 16 wherein the control module determines the level of the fluid based on a comparison of the resistance of the plurality of resistors after the plurality of resistors are energized for a predetermined period.

18. The apparatus according to claim 15 wherein the control module determines the level of the fluid when the resistance of the heating circuit exceeds a predetermined value after the heating circuit is energized for a predetermined period.

19. The apparatus according to claim 15, wherein the fluid is a urea solution.

20. The apparatus according to claim 15, further comprising a sensing circuit distinct from the heating circuit applied on the probe section for determining characteristics of the fluid.

21. A method of determining and controlling characteristics of a fluid comprising:
   energizing a layered heating circuit having a plurality of resistors at a plurality of locations corresponding to a plurality of fluid levels;
   determining a change of resistance of the layered heating circuit after the heating circuit is energized;
   determining a level of the fluid based on the change of resistance of the layered heating circuit.

22. The method according to claim 21, further comprising determining that the fluid level is below a threshold when the resistance exceeds a predetermined value.

* * * * *